(12) United States Patent
Seipel (10) Patent No.: US 11,213,561 B2
(45) Date of Patent: Jan. 4, 2022

(54) HERBAL METHODS FOR THE IMPROVEMENT OF SLEEP, SOCIAL INTERACTION, CONCERN OR WORRY

(71) Applicant: Tracey Anne Seipel, Kelvin Grove (AU)

(72) Inventor: Tracey Anne Seipel, Kelvin Grove (AU)

(73) Assignee: Rox IP Pty Ltd.

( * ) Notice: Subject to any disclaimer, the term of this patent is extended or adjusted under 35 U.S.C. 154(b) by 755 days.

(21) Appl. No.: 15/619,404

(22) Filed: Jun. 9, 2017

(65) Prior Publication Data

US 2018/0353562 A1 Dec. 13, 2018

(51) Int. Cl.
*A61K 36/899* (2006.01)
*A61K 36/185* (2006.01)
*A61K 36/11* (2006.01)
*A61K 36/54* (2006.01)

(52) U.S. Cl.
CPC ............ *A61K 36/899* (2013.01); *A61K 36/11* (2013.01); *A61K 36/185* (2013.01); *A61K 36/54* (2013.01)

(58) Field of Classification Search
None
See application file for complete search history.

(56) References Cited

U.S. PATENT DOCUMENTS

2013/0164397 A1* 6/2013 Seipel .................... A61K 36/12
424/773

* cited by examiner

*Primary Examiner* — Terry A McKelvey
*Assistant Examiner* — Catheryne Chen
(74) *Attorney, Agent, or Firm* — Steve Hassid; Partners Law Group Inc.

(57) ABSTRACT

Methods for, among other things, improving sleep, energy and social interaction and reducing concern or worry in mammals are provided. In one embodiment, the method includes administering a tablet, capsule or caplet of 190 mg to 3200 mg of compositions that include extracts of *Crateva nurvala*, *Equisetum arvense*, *Lindera aggregata*, and *Zea mays* daily.

13 Claims, 13 Drawing Sheets

FIG. 1
SLEEP

\* significantly different from the start of the trial (week 0)
significantly different from the control group

| HERB | Starting quantity of dried herb (mg) | Extract solvents (Ethanol:Water) | Extract ratio | Amount of concentrated herbal extract per capsule (mg) |
|---|---|---|---|---|
| Crateva nurvala | 3000 | 95:5 | 25:1 | 120 |
| Lindera aggregata | 1500 | 0:100 | 10:1 | 150 |
| Equisetum arvense | 1500 | 70:30 | 10:1 | 150 |
| TOTAL | | | | 420 |

FIG. 5

| HERB | Starting quantity of dried herb (mg) | Extract Solvents (Ethanol:Water) | Extract Ratio | Amount of concentrated herbal extract per capsule (mg) |
|---|---|---|---|---|
| Crateva nurvala | 2000 | 95:5 | 25:01 | 80 |
| Lindera aggregata | 1250 | 0:100 | 10:01 | 125 |
| Equisetum arvense | 1250 | 70:30 | 10:01 | 125 |
| Zea mays | 2250 | 70:30 | 10:01 | 225 |
| TOTAL | | | | 555 |

FIG. 6
SINGLE HERBS

|  | Single herb Crateva nurvala 4.5 g | Single herb Equisetum arvense (Horsetail) 2.75 g | Single herb Lindera aggregata 3.25 g | Single herb Zea mays (Cornsilk) 6 g |
|---|---|---|---|---|
| Percent Improvements in Symptom at Month 2 |  |  |  |  |
| Sleep: | 10% | 10% | 10% | 10% |
| Concern/Worry: | 0% | 3% | 0% | 6% |
| Socializing: | 5% | 5% | 8% | 0% |

|  | Single herb Crateva nurvala 20 g | Single herb Equisetum arvense (Horsetail) 12 g | Single herb Lindera aggregata 15 g | Single herb Zea mays (Cornsilk) 30 g |
|---|---|---|---|---|
| Percent Improvements in Symptom at Month 2 |  |  |  |  |
| Sleep: | 50% | 50% | 50% | 50% |
| Concern/Worry: | 12% | 15% | 0% | 9% |
| Socializing: | 16% | 12% | 16% | 0% |

|  | Single herb Crateva nurvala 50 g | Single herb Equisetum arvense (Horsetail) 35 g | Single herb Lindera aggregata 40 g | Single herb Zea mays (Cornsilk) 70 g |
|---|---|---|---|---|
| Percent Improvements in Symptom at Month 2 |  |  |  |  |
| Sleep: | 70% | 70% | 70% | 70% |
| Concern/Worry: | 15% | 15% | 10% | 10% |
| Socializing: | 18% | 15% | 18% | 8% |

FIG. 7

COMBINATION HERBS

|  | Three Herbs (Lower Dose): | Three Herbs (Middle Dose): | Three Herbs (Higher Dose): |
|---|---|---|---|
|  | Crateva nurvala: 1 g<br><br>Equisetum arvense: 0.75 g<br><br>Lindera aggregata: 0.75 g | Crateva nurvala: 6 g<br><br>Equisetum arvense: 3 g<br><br>Lindera aggregata: 3 g | Crateva nurvala: 15 g<br><br>Equisetum arvense: 9 g<br><br>Lindera aggregata: 9 g |
| Percent Improvements in Symptom at Month 2 |  |  |  |
| Sleep: | 10% | 50% | 70% |
| Concern/Worry: | 20% | 75% | 83% |
| Socializing: | 8% | 20% | 38% |
| Daily dose (dry/starting herb equivalent): | 2.5 g | 12 g | 33 g |
| Daily dose (concentrated extract): | 190 mg | 840 mg | 2400 mg |

|  | Four Herbs (Lower Dose): | Four Herbs (Middle Dose): | Four Herbs (Higher Dose): |
|---|---|---|---|
|  | Crateva nurvala: 0.8g<br><br>Equisetum arvense: 0.5g<br><br>Lindera aggregata: 0.5g<br><br>Zea mays: 1.5g | Crateva nurvala: 4 g<br><br>Equisetum arvense: 2.5 g<br><br>Lindera aggregata: 2.5 g<br><br>Zea mays: 4.5 g | Crateva nurvala: 10 g<br><br>Equisetum arvense: 6 g<br><br>Lindera aggregata: 6 g<br><br>Zea mays: 16 g |
| Percent Improvements in Symptom at Month 2 |  |  |  |
| Sleep: | 10% | 50% | 70% |
| Concern/Worry: | 17% | 55% | 65% |
| Socializing: | 9% | 35% | 42% |
| Daily dose (dry/starting herb equivalent): | 3.3 g | 13.5 g | 38 g |
| Daily dose (concentrated extract): | 282 mg | 1110 mg | 3200 mg |

FIG. 8
70%, 50% AND 10% IMPROVEMENT CALCULATIONS

Take 70% Improvement in sleep, concern or worry, and socializing as the particular result (ED50):

- Preparation A (Crateva): the ED70 is 50g → so A = 50
- Preparation B (Equisetum): the ED70 is 35g → so B = 35
- Preparation C (Lindera): the ED70 is 40g → so C = 40
- Preparation D (Zea): the ED70 is 70g → so D = 70

Four herb, an ED70 is achieved with a four-herb blend of 10g Crateva + 6g Equisetum + 6g Lindera + 16g Zea → so, a = 10; b = 6; c = 6; d = 16
Per above figures: a/A + b/B + c/C + d/D → 10/50 + 6/35 + 6/40 + 16/70 = 0.20 + 0.17 + 0.15 + 0.23 ≈ 0.75

Three herb, an ED70 is achieved with a three-herb blend of 15g Crateva + 9g Horsetail + 9g Lindera → so, a = 15; b = 9; c = 9
Per above figures: a/A + b/B + c/C + d/D → 15/50 + 9/35 + 9/40 = 0.30 + 0.26 + 0.22 ≈ 0.78

Take 50% Improvement in sleep, concern or worry, and socializing as the particular result (ED50):

- Preparation A (Crateva): the ED50 is 20g → so A = 20
- Preparation B (Equisetum): the ED50 is 12g → so B = 12
- Preparation C (Lindera): the ED50 is 15g → so C = 15
- Preparation D (Zea): the ED50 is 30g → so D = 30

Four herb, an ED50 is achieved with a four-herb blend of 4g Crateva + 2.5g Equisetum + 2.5g Lindera + 4.5g Zea → so, a = 4; b = 2.5; c = 2.5; d = 4.5
Per above figures: a/A + b/B + c/C + d/D → 4/20 + 2.5/12 + 2.5/15 + 4.5/30 = 0.20 + 0.21 + 0.17 + 0.15 = 0.73

Three-herb, an ED50 is achieved with a three-herb blend of 6g Crateva + 3g Horsetail + 3g Lindera → so a = 6; b = 3; c = 3
Per above figures: a/A + b/B + c/C = 6/20 + 3/12 + 3/15 = 0.30 + 0.25 + 0.20 = 0.75

Take 10% Improvement in sleep, concern or worry, and socializing as the particular result (so ED10):

- Preparation A (Crateva): the ED10 is 4.5g → so A = 4.5
- Preparation B (Equisetum): the ED10 is 2.75g → so B = 2.75
- Preparation C (Lindera): the ED10 is 3.25g → so C = 3.25
- Preparation D (Zea): the ED10 is 6g → so D = 6

Four herb, an ED10 is achieved with a four-herbal blend of 0.8g Crateva + 0.5g Equisetum + 0.5g Lindera + 1.5g Zea → so, a = 0.8; b = 0.5; c = 0.5; d = 1.5
Per above figures: a/A + b/B + c/C + d/D → 0.8/4.5 + 0.5/2.75 + 0.5/3.25 + 1.5/6 = 0.18 + 0.18 + 0.15 + 0.25 ≈ 0.76

Three-herb, an ED10 is achieved with a three-herb herbal blend of 1g Crateva + 0.75g Horsetail + 0.75g Lindera → so a = 1; b = 0.75; c = 0.75
Per above figures: a/A + b/B + c/C = 1/4.5 + 0.75/2.75 + 0.75/3.25 = 0.22 + 0.27 + 0.23 = 0.72 (with exact rounding = 0.73)

FIG. 9
SLEEP ONSET (TOTAL AVERAGE)

FIG. 10
SLEEP MAINTENANCE (TOTAL AVERAGE)

FIG. 11

ENERGY (TOTAL AVERAGE)

FIG. 12

| 10% Improvement | | | | | | | | | |
|---|---|---|---|---|---|---|---|---|---|
| Combination | Ingred: #1 | Dose (g) | Ingred: #2 | Dose (g) | Ingred: #3 | Dose (g) | Ingred: #4 | Dose (g) | ED 10 calculation |
| A | A | 4.5 | | | | | | | |
| B | B | 2.75 | | | | | | | |
| C | C | 3.25 | | | | | | | |
| D | D | 6 | | | | | | | |
| A + B | A | 2 | B | 1.55 | | | | | 1.01 |
| A + C | A | 2 | C | 2 | | | | | 1.06 |
| A + D | A | 2 | D | 3.5 | | | | | 1.03 |
| B + C | B | 1.5 | C | 2.5 | | | | | 1.31 |
| B + D | B | 1.5 | D | 2.75 | | | | | 1.00 |
| C + D | C | 2.5 | D | 2.5 | | | | | 1.19 |
| A + B + C | A | 1 | B | 0.75 | C | 0.75 | | | 0.73 |
| A + C + D | A | 1.5 | C | 1 | D | 2.25 | | | 1.02 |
| B + C + D | B | 1 | C | 1 | D | 2.25 | | | 1.05 |
| A + B + D | A | 1.5 | B | 1 | D | 2.50 | | | 1.11 |
| A + B + C + D | A | 0.8 | B | 0.5 | C | 0.5 | D | 1.5 | 0.76 |

A = Crateva nurvala
B = Equisetum arvense
C = Lindera aggregata
D = Zea mays

FIG. 13

| 50% Improvement | | | | | | | | | |
|---|---|---|---|---|---|---|---|---|---|
| Combination | Ingred: #1 | Dose (g) | Ingred: #2 | Dose (g) | Ingred: #3 | Dose (g) | Ingred: #4 | Dose (g) | ED 50 calculation |
| A | A | 20 | | | | | | | |
| B | B | 12 | | | | | | | |
| C | C | 15 | | | | | | | |
| D | D | 30 | | | | | | | |
| A + B | A | 9 | B | 7 | | | | | 1.03 |
| A + C | A | 9 | C | 10 | | | | | 1.12 |
| A + D | A | 9 | D | 18 | | | | | 1.05 |
| B + C | B | 8 | C | 10 | | | | | 1.33 |
| B + D | B | 7.5 | D | 18 | | | | | 1.23 |
| C + D | C | 10 | D | 16 | | | | | 1.20 |
| A + B + C | A | 6 | B | 3 | C | 3 | | | 0.75 |
| A + C + D | A | 7.5 | C | 4.5 | D | 12.5 | | | 1.09 |
| B + C + D | B | 4.5 | C | 5 | D | 12 | | | 1.11 |
| A + B + D | A | 7.5 | B | 5 | D | 12 | | | 1.19 |
| A + B + C + D | A | 4 | B | 2.5 | C | 2.5 | D | 4.5 | 0.73 |

A = Crateva nurvala
B = Equisetum arvense
C = Lindera aggregata
D = Zea mays

FIG. 14

| 70% Improvement | | | | | | | | | |
|---|---|---|---|---|---|---|---|---|---|
| Combination | Ingred: #1 | Dose (g) | Ingred: #2 | Dose (g) | Ingred: #3 | Dose (g) | Ingred: #4 | Dose (g) | ED 70 calculation |
| A | A | 50 | | | | | | | |
| B | B | 35 | | | | | | | |
| C | C | 40 | | | | | | | |
| D | D | 70 | | | | | | | |
| A + B | A | 25 | B | 18 | | | | | 1.01 |
| A + C | A | 25 | C | 20 | | | | | 1.00 |
| A + D | A | 25 | D | 38 | | | | | 1.04 |
| B + C | B | 18 | C | 22 | | | | | 1.06 |
| B + D | B | 20 | D | 40 | | | | | 1.14 |
| C + D | C | 22 | D | 40 | | | | | 1.12 |
| A + B + C | A | 15 | B | 9 | C | 9 | | | 0.78 |
| A + C + D | A | 15 | C | 16 | D | 30 | | | 1.13 |
| B + C + D | B | 14 | C | 16 | D | 30 | | | 1.23 |
| A + B + D | A | 15 | B | 10 | D | 30 | | | 1.01 |
| A + B + C + D | A | 10 | B | 6 | C | 6 | D | 16 | 0.75 |

A = Crateva nurvala
B = Equisetum arvense
C = Lindera aggregata
D = Zea mays

HERBAL METHODS FOR THE IMPROVEMENT OF SLEEP, SOCIAL INTERACTION, CONCERN OR WORRY

FIELD OF THE DISCLOSURE

This disclosure generally relates to methods to improve sleep and social interaction, to reduce concern or worry, and to increase energy.

General Background

Poor sleep, concern, worry and difficulties with social interactions are common issues affecting large numbers of the population in the twenty-first century. Behavioural and lifestyle changes can improve these problems. Anxiolytic, anti-depressant and sedative medications may be prescribed. It is considered that the increasing use of recreational drugs and alcohol may be due to, at least in part, self-medication to reduce worry and help the individual to relax in social situations.

Herbal medications with anxiolytic, sedative, and hypnotic effects have been shown to be effective in improving sleep, worry, and social interactions, including nervine herbs such as Valerian, Skullcap, Vervain, Passionflower; and adaptogenic herbs such as *Ginseng, Withania, Rhodiola* and *Eleutherococcus*.

This study assessed the efficacy of a combination of phytomedicine extracts including, *Crateva nurvala* bark of the stem and/or root, *Equisetum arvense* stem (Horsetail), and *Lindera aggregata* root, in reducing symptoms of worry and anxiety, and improving sleep and socialising.

This combination has been shown to be effective in reducing symptoms of urinary urgency, frequency, incontinence and nocturia. Local administration of *Lindera aggregata* can help with circulation and muscle relaxation and systemically *Lindera* has also been shown to reduce inflammation and improve joint pain (Bensky D, Gamble A. Chinese Herbal Materia Medica. Revised ed. Washington Eastland Press; 1993.). Whilst traditional evidence for *Equisetum arvense* (Horsetail) and *Crateva nurvala* does not indicate improvements in sleep and emotional health. (BHP. British Herbal Pharmacopeia. West Yorks, UK.: British Herbal Medicine Association; 1983; Bone K. Clinical Applications of Ayurvedic and Chinese Herbs; Monographs for the Western Herbal Practitioner. Warwick, Australia: Phytotherapy Press; 1997.), *Crateva nurvala* is also known to reduce inflammation (Bone) and, with *Lindera aggregata*, may assist in reducing joint pain. Additionally, research had shown *Crateva nurvala* can affect electrolyte levels with increased retention of calcium and increased expulsion of sodium and magnesium, with a reduction in renal urolithiasis. The subsequent change in electrolyte status, with the anti-inflammatory and muscle tonic effect of *Crateva nurvala* may have an impact on emotional health and sleep.

SUMMARY

A randomised, double-blind, placebo controlled trial assessed the effect of different herbal combinations of *Crateva nurvala* bark, *Equisetum arvense* stem and *Lindera aggregata* root in improving sleep, reducing concern or worry and improving social interactions. 150 participants were interviewed at two primary care centres at baseline and after 8 weeks of treatment.

Furthermore, a randomised, double-blind, placebo controlled trial was also performed to assess the effect of different herbal combinations of *Crateva nurvala* bark, *Equisetum arvense* stem, *Lindera aggregata* root, and *Zea mays* stylus to improve sleep, reduce concern or worry, improve social interactions and increase energy.

The treatments were well tolerated with no significant side effects observed, resulting in withdrawal from treatment. Two herbal combination(s) in particular resulted in participants experiencing statistically significant and synergistic improvement in the amount and quality of their sleep; reduced concern and worry; improved social interactions; and increased energy over 8 weeks of treatment.

DRAWINGS

FIG. 8 shows 70%, 50%, and 10% improvement calculations for the indicated single herbs and combination of herbs indicated.

DETAILED DESCRIPTION 150 adults recruited from Brisbane holistic clinics and evenly divided into active (35 males; 40 females) and placebo (27 males and 48 females) arms, with an average age of 63.5 years and weight of 78.8 kg commenced the study.

All participants responded they were bothered by lack of sleep, worry, or had socializing concerns. Participants were not currently pregnant or breast feeding; were not using medications including unregulated doses of diuretics and bladder medications; were not undergoing treatment for mental health issues or psychotic disturbances; had not undergone recent surgery such as hysterectomy or prostatectomy; did not have uncontrolled diabetes, mellitus, heart disease, pancreatic, hepatic or renal disease, neurologic disease, recurrent urinary tract infections, benign prostatic hypertrophy and chronic inflammatory conditions.

The treatment protocol consisted of ingesting daily for a period of 8-weeks, the two (2) capsules, containing, per capsule, a 420 mg blend of various formulations indicated herein containing *Crateva nurvala, Equisetum arvense*, and *Lindera aggregata* or a color matched vegetarian capsule placebo containing color-matched cellulose. Range of 190 mg to 2400 mg of the various formulations indicated here were also tested and demonstrated efficacy. Identity of the extracts were confirmed prior to manufacture of the finished capsule via high performance thin layer chromatography and capsules were manufactured in a Therapeutic Goods Administration licensed facility according to the PIC/S Guide to Good Manufacturing Practice for Medicinal Products, PE 009-9-15 Jan. 2009. The efficacy of the treatment on sleep, concern, worry, and social interaction was assessed by measuring responses to questions in the following areas:

Sleep
1) They did not get the amount of sleep they needed?
2) They felt they were unable to get a good night's rest?
3) Did they wake in the night from sleep?

Concern/Worry
1) They felt like there was something wrong with them?
2) Did they experience embarrassment?

Social Interaction
1) Were there concerns with their relationships with family and friends?
2) Did they have problems with their partner or spouse?

Participant's responses to these questions were asked on a 6-point scale with responses rated from 1 to 6 as: (1) not at all; (2) a little bit; (3) somewhat; (4) quite a bit; (5) a great deal; (6) a very great deal.

Participants meeting the above criteria, provided written informed consent and were randomised by a third party, via block of four method, into either treatment or placebo. Both participants and researchers remained blinded to treatment allocation until after completion of statistical analysis.

All comparisons for the two treatments (as change from baseline) were made using mixed effects ordered logistic regression adjusted for repeated measures. Holm estimation test was used to adjust p-values for repeated measures.

Baseline demographic and symptom characteristics of placebo and treatment groups were similar between the two groups.

Figure 1:
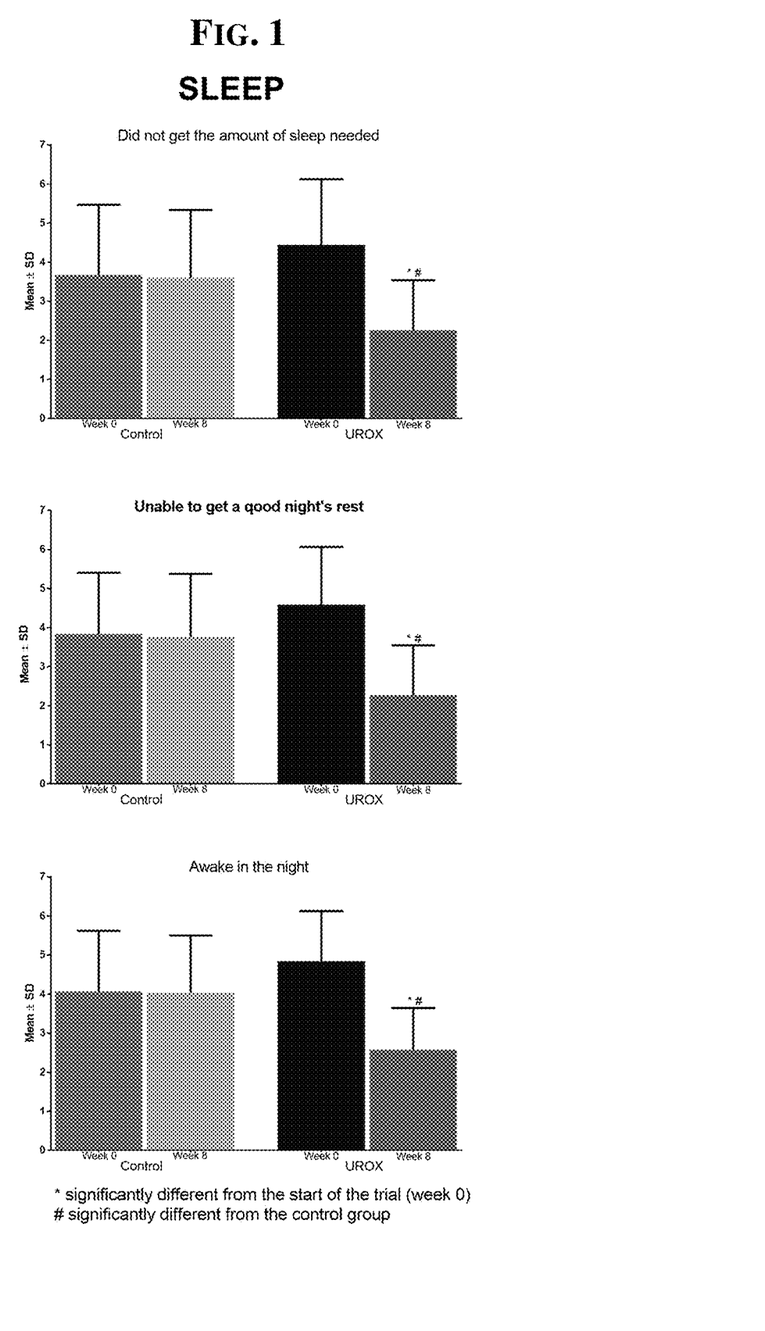
FIG. 1 shows sleep results from the study described herein with the standard deviation (SD).
Figure 2:
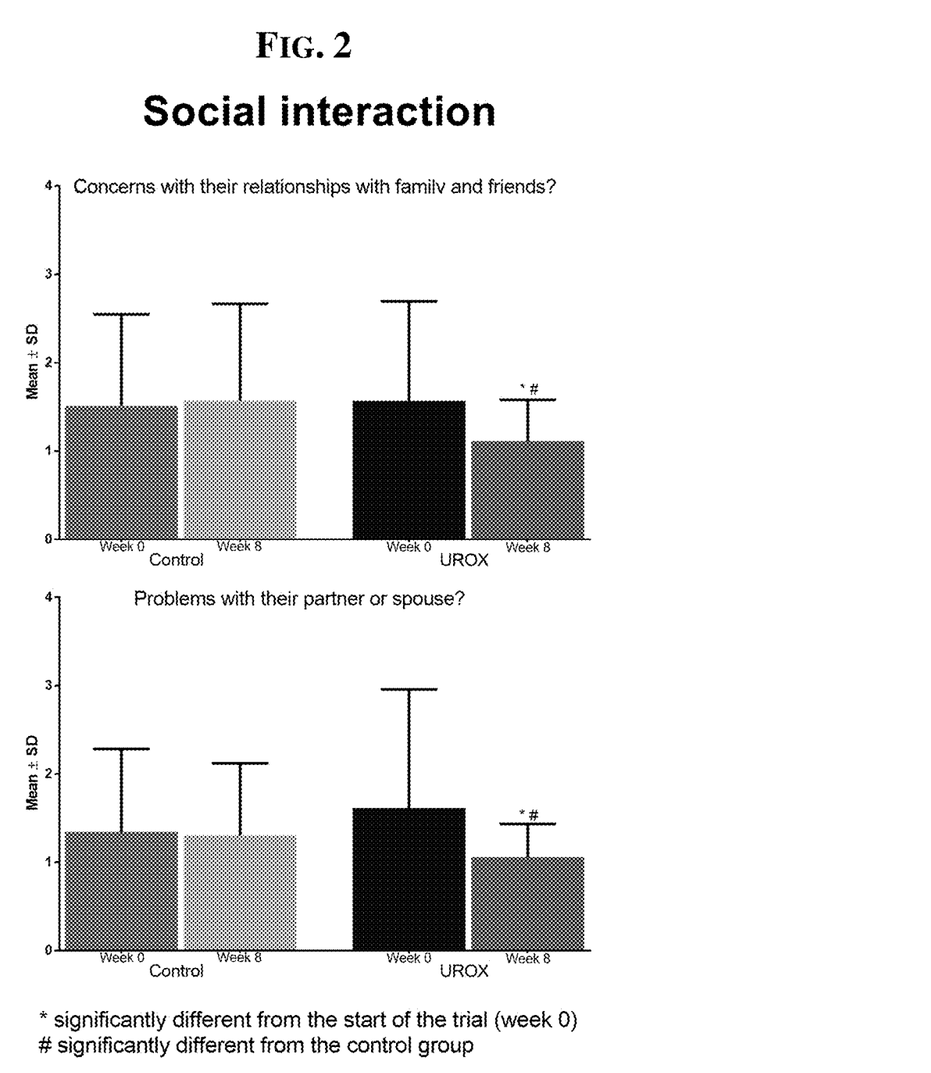
FIG. 2 shows social interaction results from the study described herein with the standard deviation.
Figure 3:
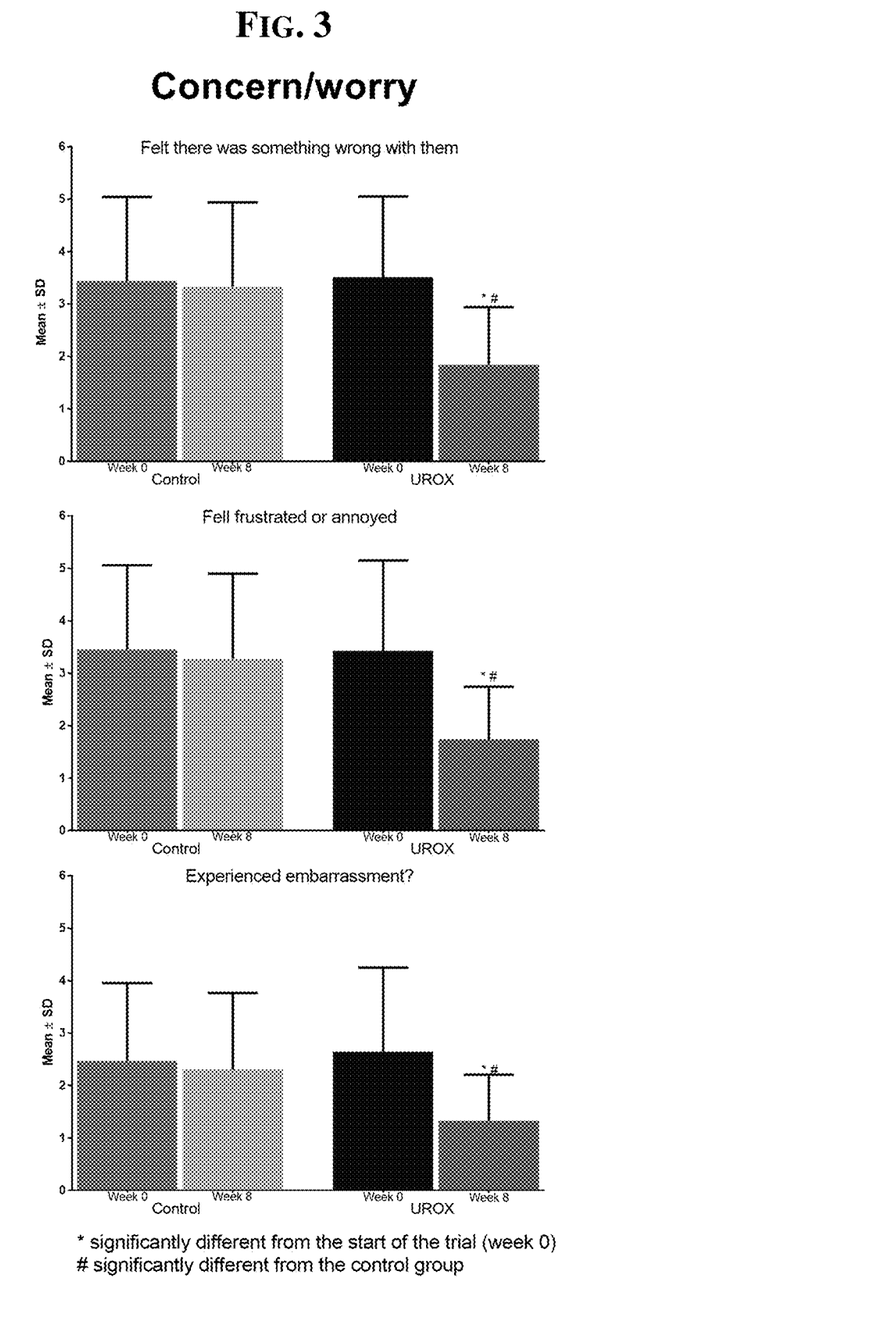
FIG. 3 shows concern or worry results from the study described herein with the standard deviation.

Significant improvements (i.e. reductions), were observed from the start of the study to the end of the trial (week 8) in scores for all questions including sleep; concern or worry; and social interaction; in the active group compared to the control group. Mean scores for each of the measures are shown in FIGS. 1, 2 and 3. Furthermore, FIGS. 1, 2 and 3 display the standard deviations (SD), which demonstrates the measurement for the group spread out from the average (mean), illustrated by the bars on the graph. The standard deviation is denoted below using the +/− sign. The standard deviation was determined by providing a mean value for a series of values, in which the difference between the value and the mean value was calculated for each of the values of the group. Lastly, the weighted differences are summed and divided by an appropriate predetermined number to obtain the group spread from the average.

At the start of the trial, over fifty percent of the completed participants (73 in control and 69 in treatment group) reported a score of 4 and above (with SD of +/−1.6; maximum score 6) for sleep-related measures (For instance, 1. Did not get the amount of sleep needed; 2. Unable to get a good night's rest; and 3. Awoke in the night). While the results did not change for the control group, fifty percent of the patients in the active group reported a score of 2 or less (with SD of +/−1.7) by the end of the trial (FIG. 1.)

The results for social interaction measures showed improvement/reduction in the final score in the treatment group, as shown in FIG. 2. (For instance, 1. Concerns with their relationships with family and friends; and 2. Problems with their partner or spouse.) The median score for the control group remained 1 (with SD of +/−0.9) from the start to the end of the trial; however, the maximum score changed by 2 points (with SD of +/−0.5; 6 at start and 4 at completion of the trial) for the treatment group, suggesting an improvement in the parameter measured.

Similar improvements were observed for the concern or worry measures, as shown in FIG. 3 (For instance, 1. Felt there was something wrong with them; 2. Fell frustrated or annoyed; and 3. Experienced embarrassment.). While the median and mean scores remained same from the start to the end of the trial for the control group, the treatment group showed reductions in scores with fifty percent of the patients giving the score of 1 or less (with SD of +/−1.2) at the end of the trial compared to the score of 4 (with SD of +/−1.4) at the start of the trial.

Figure 4:
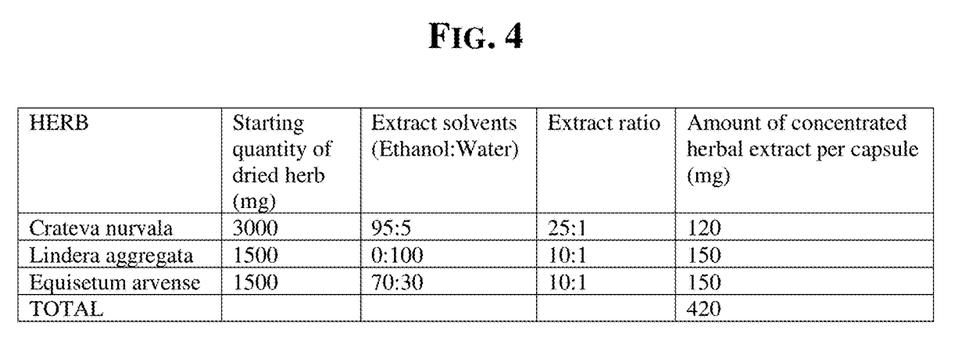
FIG. 4 shows the dosage level of the three-herb combination for one embodiment of the present disclosure tested in the study described herein.

As shown in FIG. 4, the specific exemplary dosage levels of the three-herb combination is shown as one embodiment. Dried weight of 3000 mg of *Crateva nurvala* is reduced using 95% ethanol and 5% water to an extract ratio of 25 to 1 for a concentrated herbal extract weight of 120 mg. Dried weight of 1500 mg of *Lindera aggregata* is reduced using 100% water to an extract ratio of 10 to 1 for a concentrated herbal extract weight of 150 mg. Dried weight of 1500 mg of *Equisetum arvense* is reduced using 70% ethanol and 30% water to an extract ratio of 10 to 1 for a concentrated herbal extract weight of 150 mg. In at least this embodiment, the extract solvents used were ethanol and water.

In another yet embodiment, other solvents known in the industry to produce similar results can be used as well.

In yet another embodiment, the ratios could be selected from the group including, but not limited to, 90:10, 85:15, 80:20, 75:25, 65:35, 60:40, 55:45 and 50:50.

In yet another embodiment, the extracts were 25:1 and 10:1.

In yet another embodiment, the extract ratio is 20:1.
In yet another embodiment, the extract ratio is 15:1.
In yet another embodiment, the extract ratio is 5:1.

The ingredients of the present invention, for the three herb combination, work synergistically to provide the benefits and advantages discussed herein. One way that synergy can be proven is using the median-effect equation:

$$CI = \sum_{j=1}^{n} \frac{(D)_j}{(Dx)_j}$$

(See Tallarida, Ronald J., "Quantitative Methods for Assessing Drug Synergism", Genes & Cancer 2(11) 1003-1008 (Jan. 24, 2012); see also, Chou, Ting-Chao, "Drug Combination Studies and Their Synergy Quantification Using the Chou-Talalay Method", Cancer Res. 70(2) (Jan. 15, 2010); see also, Breitinger, Hans-Georg, "Drug Synergy—Mechanisms and Methods of Analysis", 159, Toxicity and Drug Testing (Feb. 10, 2012)).

In this equation, the quantity of an individual ingredient as used in combination with all ingredients to achieve a given result is divided by the quantity of an individual ingredient as used by itself to achieve the same given result. If the equation equals less than 1, then the composition is synergistic. (See Breitinger at Page 159).

Figure 6:
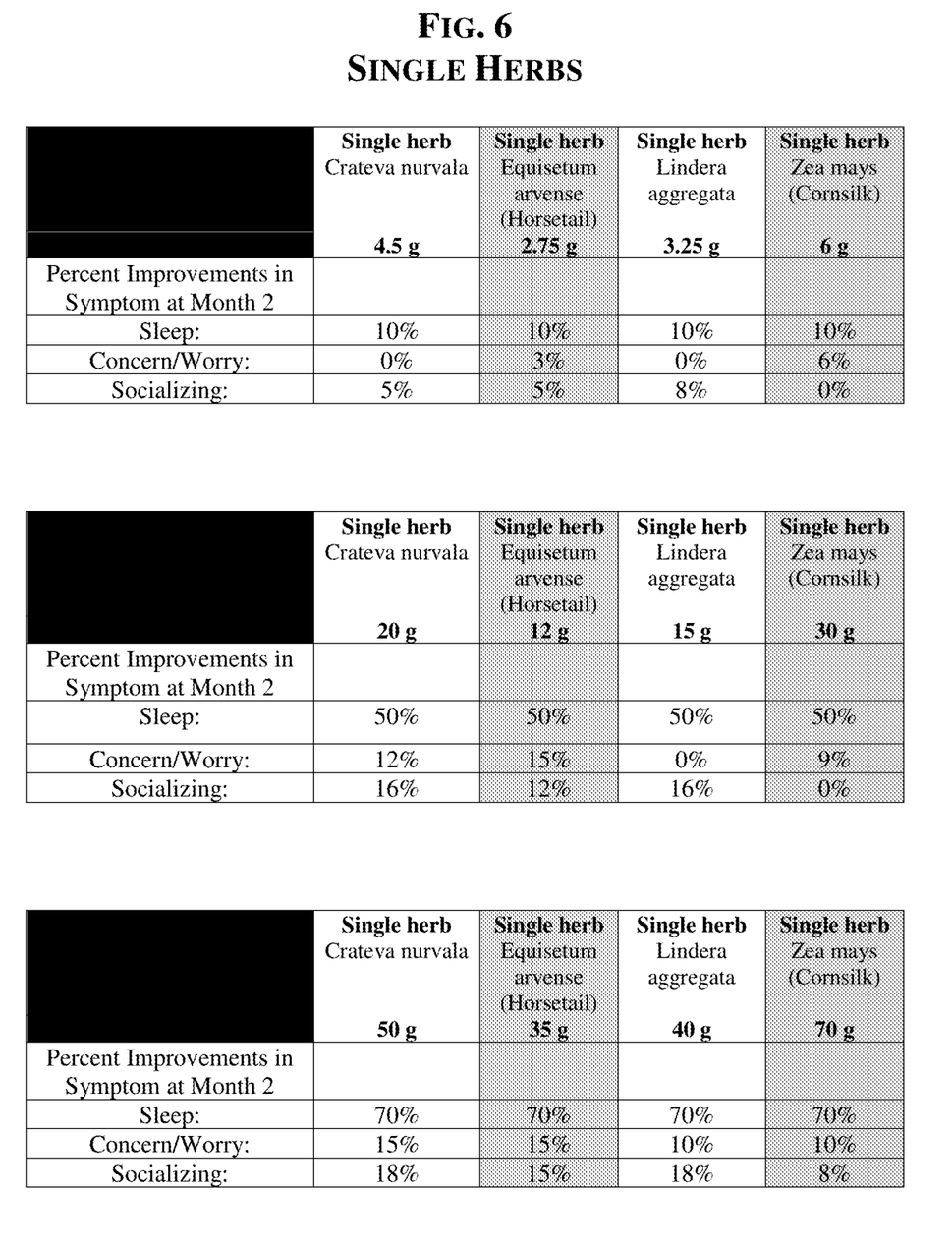
FIG. 6 shows the dosage levels that achieve the indicated percent improvement in symptoms for indicated single herbs.
Figure 7:
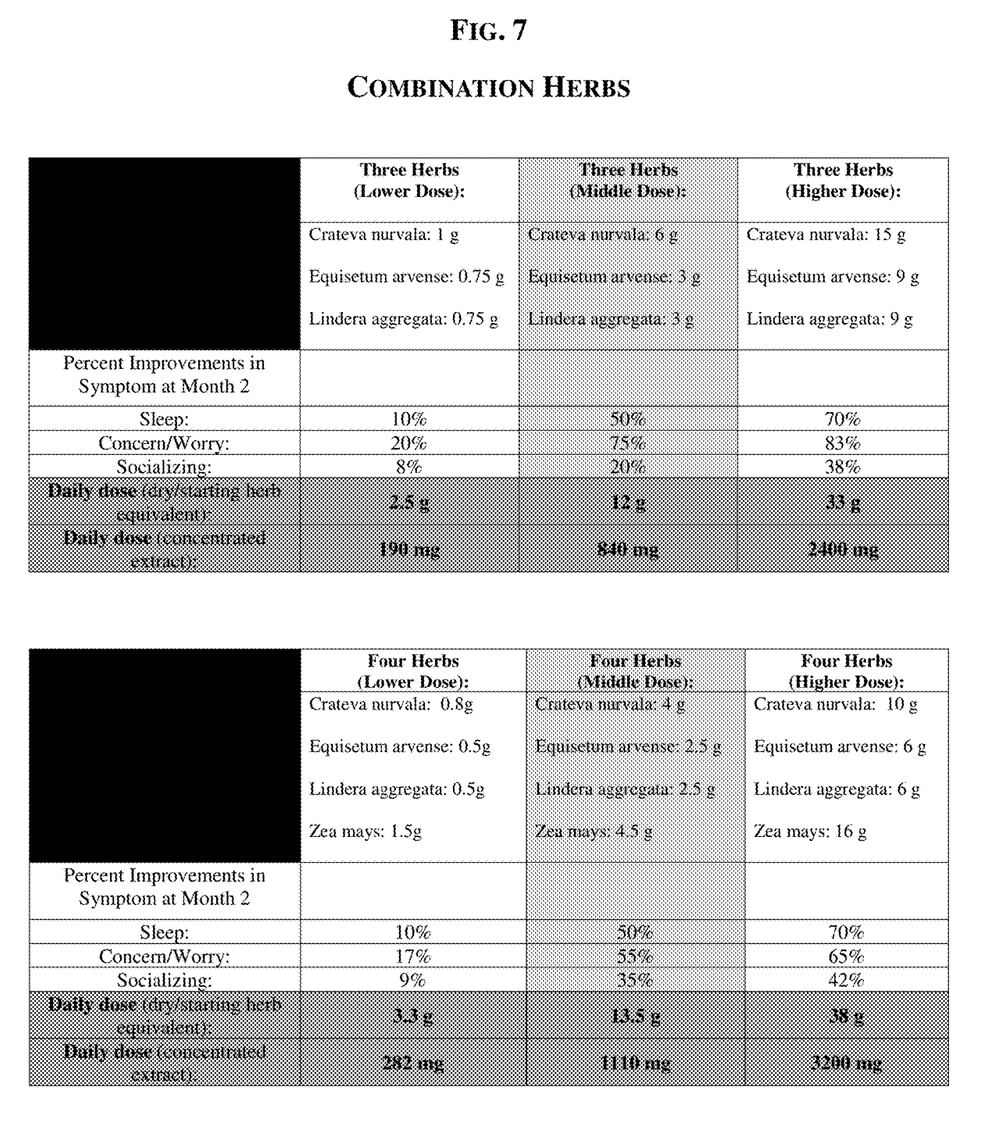
FIG. 7 shows the dosage levels that achieve the indicated percent improvement in symptoms for combination of herbs indicated.

To achieve a 70% improvement in sleep, concern or worry, and socializing, as illustrated in FIGS. 6 and 7 for the three herb combination, 33 g of dry weight equivalence of the blend per capsule was used, where 15 g was *Crateva nurvala*, 9 g was *Lindera aggregata*, and 9 g was *Equisetum arvense*. Individually, to achieve the same result of 70% improvement in sleep, concern or worry, and socializing, 50 g *Crateva nurvala* was needed, 35 g of *Equisetum arvense* was needed, and 40 g of *Lindera aggregata* was needed. Applying these numbers into the median-effect equation, 15/50+9/35+9/40=0.78. This number is less than 1, so the composition is synergistic. These individual herbs were tested to determine the individual dosages required to produce the effect of 70% improvement in sleep; however, these individual dosages are in excess of recommended dosages that are believed to be safe for long term use and are not recommended for long term use.

To achieve a 50% improvement in sleep, concern or worry, and socializing, as illustrated in FIGS. 6 and 7 for the three herb combination, 12 g of dry weight equivalence of the blend per capsule was used, where 6 g was *Crateva nurvala*, 3 g was *Lindera aggregata*, and 3 g was *Equisetum arvense*. Individually, to achieve the same result of 50% improvement in sleep, concern or worry, and socializing, 20 g *Crateva nurvala* was needed, 12 g of *Equisetum arvense* was needed, and 15 g of *Lindera aggregata* was needed. Applying these numbers into the median-effect equation, 6/20+3/12+3/15=0.75. This number is less than 1, so the composition is synergistic. These individual herbs were tested to determine the individual dosages required to produce the effect of 50% improvement in sleep, concern or worry, and socializing; however, these individual dosages are in excess of recommended dosages that are believed to be safe for long term use and are not recommended for long term use.

To achieve a 10% improvement in sleep, concern or worry, and socializing, as illustrated in FIGS. 6 and 7 for the three herb combination, 2.5 g of dry weight equivalence of the blend per capsule was used, where 1 g was *Crateva nurvala*, 0.75 g was *Lindera aggregata*, and 0.75 g was *Equisetum arvense*. Individually, to achieve the same result of 10% improvement in sleep, concern or worry, and socializing, 4.5 g *Crateva nurvala* was needed, 2.75 g of *Equisetum arvense* was needed, and 3.25 g of *Lindera aggregata* was needed. Applying these numbers into the median-effect equation, 1/4.5+0.75/2.7+0.75/3.25=0.73. This number is less than 1, so the composition is synergistic.

As the results herein demonstrate, in one embodiment, the *Crateva nurvala*, *Equisetum arvense* and *Lindera aggregata* combination, after 8 weeks of treatment, resulted in statistically significant reductions in concern and worry by an average of fifty percent. Reductions were seen in responses to feeling there is something wrong with them (reduced by 46%; from 3.5 to 1.9); feeling frustrated or annoyed (reduced by 49%; from 3.5 to 1.8) and experiencing embarrassment (reduced by 54%; from 2.8 to 1.3). The three herb combination also showed an average of 51% improvement in sleep as seen by responses to whether they got the amount of sleep they needed (52% improvement; from 4.4 to 2.1 response), whether they were unable to get a good night's rest (52% improvement; from 4.8 to 2.3) and whether they awoke in the night (49% improvement from 4.9 to 2.5). Social interactions also improved by an average of 36%. The total average scores for concerns with relationships with family and friends reduced by 33% (from 1.5 to 1.0) and a 38% reduction was seen with responses to problems with their partner or spouse (1.6 to 1.0).

In yet another embodiment, the four herb combination of *Crateva nurvala* bark, *Equisetum arvense* (Horsetail) stem, *Lindera aggregata* root and *Zea mays* (Cornsilk) stylus was tested using the same parameters as the three herb combination above. The results of the experiments using the four herb composition, as shown in the data in FIGS. 9-11, demonstrated statistically significant improvement in sleep onset, sleep maintenance and increase in energy levels.

Figure 5:
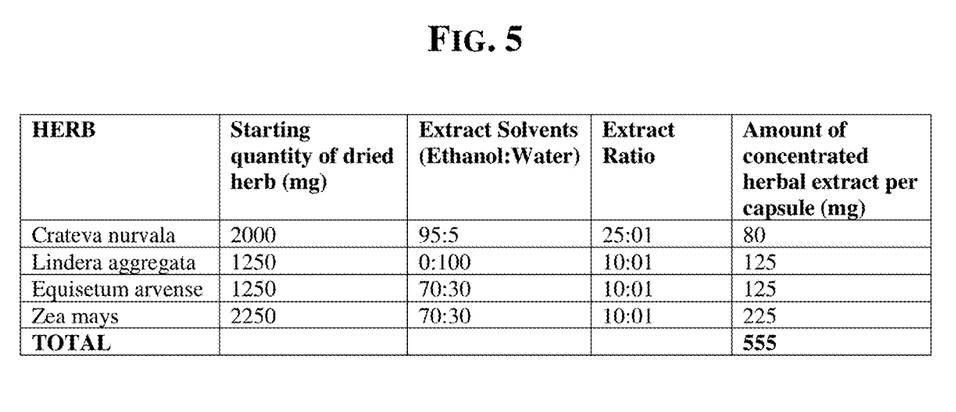
FIG. 5 shows the dosage level of the four-herb combination for one of the embodiments of the present disclosure in the study described herein.

As shown in FIG. 5 the dosage levels of the four herb combination is shown as one embodiment. Dried weight of 2000 mg of *Crateva nurvala* was reduced using 95% ethanol and 5% water to an extract ratio of 25 to 1 for a concentrated herbal extract weight of 80 mg. Dried weight of 1250 mg of *Lindera aggregata* was reduced using 100% water to an extract ratio of 10 to 1 for a concentrated herbal extract weight of 125 mg. Dried weight of 1250 mg of *Equisetum arvense* was reduced using 70% ethanol and 30% water to an extract ratio of 10 to 1 for a concentrated herbal extract weight of 125 mg. Dried weight of 2250 mg of *Zea mays* was reduced using 70% ethanol and 30% water to an extract ratio of 10 to 1 for a concentrated herbal extract weight of 225 mg. In this embodiment, the extract solvents used were ethanol and water.

It should be appreciated that other solvents known in the art can be used with any of the various embodiments described herein.

In yet another embodiment *Crateva nurvala* can be standardized with diosgenin, lupenone, lupeol, tannin, and/or cadabicine.

In yet another embodiment, *Equisetum arvense* can be standardized by silica and/or caffeic acid.

In yet another embodiment *Lindera aggregata* can be standardized by borneol, linderalactone, linderene, and/or linderazulene.

In yet another embodiment, *Zea mays* can be standardized by maizeric acid.

The results of the claimed compositions of the present disclosure, for the four herb combination, work synergistically to provide the benefits and advantages discussed herein. As discussed above, synergy can be proven using the median-effect equation:

$$CI = \sum_{j=1}^{n} \frac{(D)_j}{(Dx)_j}$$

In this equation, the quantity of an individual ingredient as used in combination with all ingredients to achieve a given result is divided by the quantity of an individual ingredient as used by itself to achieve the same given result. If the equation equals less than 1, then the composition is synergistic. (See Breitinger at Page 159).

FIGS. 6, 7, and 8 indicate the data from various herbal compositions and dosages that demonstrated 70%, 50% and 10% improvements in sleep, concern or worry, and socializing.

To achieve a 70% improvement in sleep, concern or worry, and socializing, as illustrated in FIGS. 6 and 7 for the four herb combination, 38 g of dry weight equivalence of the blend per capsule was used, where 10 g was *Crateva nurvala*, 6 g was *Equisetum arvense* (Horsetail), 6 g was *Lindera aggregata*, and 16 g was *Zea mays* (Cornsilk). Individually, to achieve the same result of 70% improvement in sleep, concern or worry, and socializing, 50 g of *Crateva nurvala* was needed, 35 g of *Equisetum arvense* (Horsetail) was needed, 40 g of *Lindera aggregata* was needed, and 70 g of *Zea mays* (Cornsilk) was needed. Applying these numbers into the median-effect equation, 10/50+6/35+6/40+16/70=0.75, gives a number less than 1, which makes the composition synergistic.

To achieve a 50% improvement in sleep, concern or worry, and socializing, as illustrated in FIGS. 6 and 7 for the four herb combination, 13.5 g of dry weight equivalence of the blend per capsule was used, where 4 g was *Crateva nurvala*, 2.5 g was *Equisetum arvense* (Horsetail), 2.5 g was *Lindera aggregata*, and 4.5 g was *Zea mays* (Cornsilk). Individually, to achieve the same result of 50% improvement in sleep, concern or worry, and socializing, 20 g of *Crateva nurvala* was needed, 12 g of *Equisetum arvense* (Horsetail) was needed, 15 g of *Lindera aggregata* was needed, and 30 g of *Zea mays* (Cornsilk) was needed. Applying these numbers into the median-effect equation, 4/20+2.5/12+2.5/15+4.5/30=0.73, gives a number less than 1, which makes the composition synergistic.

To achieve a 10% improvement in sleep, concern or worry, and socializing, as illustrated in FIGS. 6 and 7 for the four herb combination, 3.3 g of dry weight equivalence of the blend per capsule was used, where 0.8 g was *Crateva nurvala*, 0.5 was *Equisetum arvense* (Horsetail), 0.5 g was *Lindera aggregata*, and 1.5 g was *Zea mays* (Cornsilk). Individually, to achieve the same result of 10% improvement in sleep, concern or worry, and socializing, 4.5 g of *Crateva nurvala* was needed, 2.75 g of *Equisetum arvense* (Horsetail) was needed, 3.25 g of *Lindera aggregata* was needed and 6 g of *Zea mays* (Cornsilk) was needed. Applying these numbers into the median-effect equation, 0.8/4.5+0.5/2.75+0.5/3.25+1.5/6=0.76, gives a number less than 1, which makes the composition synergistic.

Trials

The four herb composition, which includes *Crateva nurvala* bark, *Equisetum arvense* (Horsetail) stem, *Lindera aggregata* root and *Zea mays* (Cornsilk) stylus (as shown in FIG. 5) was used in a clinical trial to show how it can improve sleep onset, sleep maintenance and increase of energy levels in subjects that took the composition. The participants were interviewed at baseline and after 8 weeks of the herbal treatment. The participants experienced statistically significant improvement in sleep onset, sleep maintenance and increase in energy levels.

The treatment protocol, using the four herb combination, consisted of ingesting daily for a period of 8-weeks, the two (2) capsules, containing, per capsule, a 555 mg blend of various formulations indicated herein containing *Crateva nurvala, Equisetum arvense, Lindera aggregata*, and *Zea mays* or a color matched vegetarian capsule placebo containing color-matched cellulose. Range of 282 mg to 3200 mg of the various formulations indicated herein were also tested and determined to have not been as effective as the 555 mg blend.

Patients and Methods

Participants in this study were individuals suffering from poor sleep. The participants were not currently pregnant or breast feeding; were not undergoing treatment for mental health issues or psychotic disturbances; had not undergone recent surgery such as hysterectomy or prostatectomy, did not have uncontrolled diabetes mellitus, heart disease, pancreatic, hepatic, or renal disease, neurological disease, recurrent urinary tract infections, benign prostatic hypertrophy and chronic inflammatory conditions.

The treatment protocol consisted of ingesting two capsules daily for a period of 8 weeks, containing the four herb blends for a total daily intake of 4 grams of *Crateva nurvala*, 2.5 grams of *Equisetum arvense* (Horsetail), 2.5 grams of *Lindera aggregata* and 4.5 grams of *Zea mays* (Cornsilk).

The efficacy of the treatment on sleep was assessed by recording how long it took to fall asleep (i.e., sleep onset, measured in minutes), the number of times they awoke throughout the night (i.e., sleep maintenance) and their energy (rated on a ten-point scale, from one to ten, with ten being the best energy score). Participants recorded these values for 3 days at the start of the trial, at 4 weeks and at the end of the 8-week trial period.

Results

The 12 adult participants were interviewed at baseline, after 4 weeks and 8 weeks of treatment. The (four) herb combination resulted in participants experiencing statistically significant improvements in sleep onset, sleep maintenance and increased energy levels.

Figure 9:
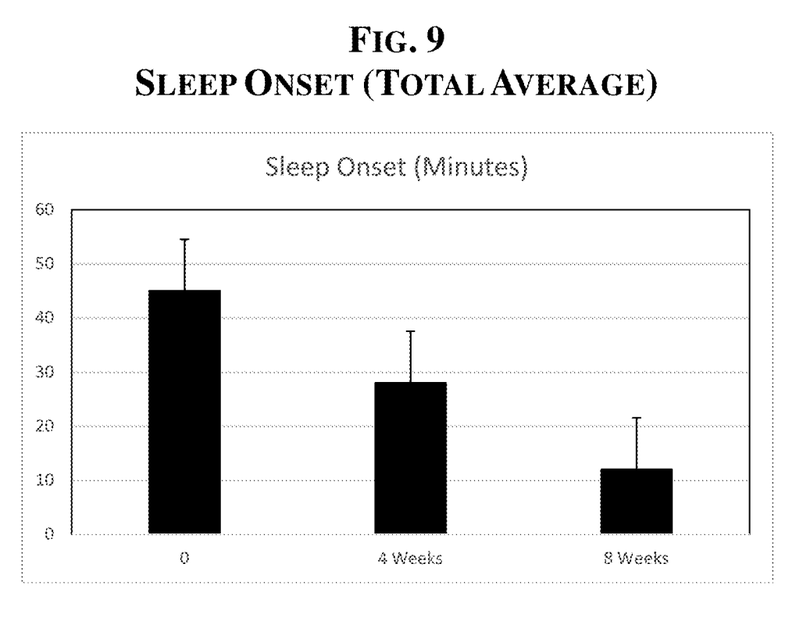
FIG. 9 shows sleep onset (total average) results from the study of the four herb combination stated herein with standard deviations.
Figure 10:
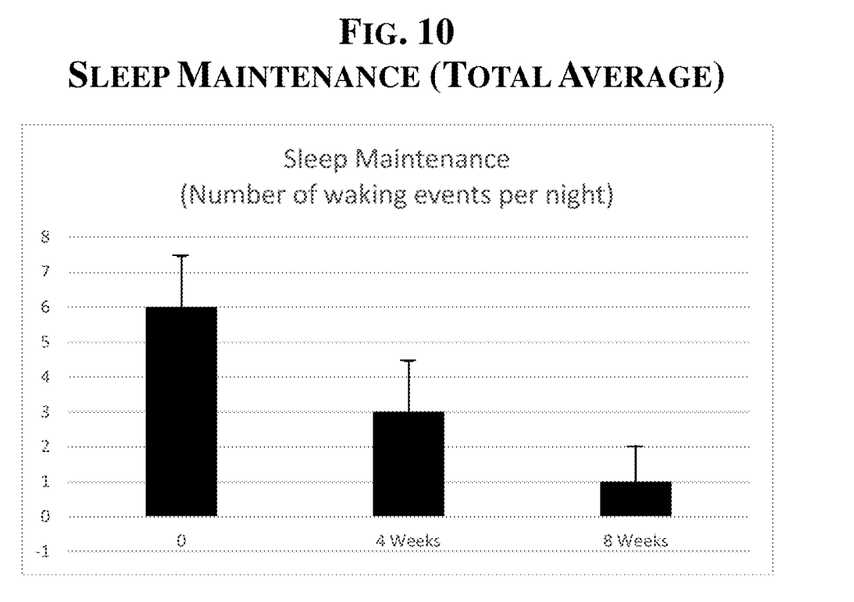
FIG. 10 shows sleep maintenance (total average) results from the study of the four herb combination stated herein with standard deviations.
Figure 11:
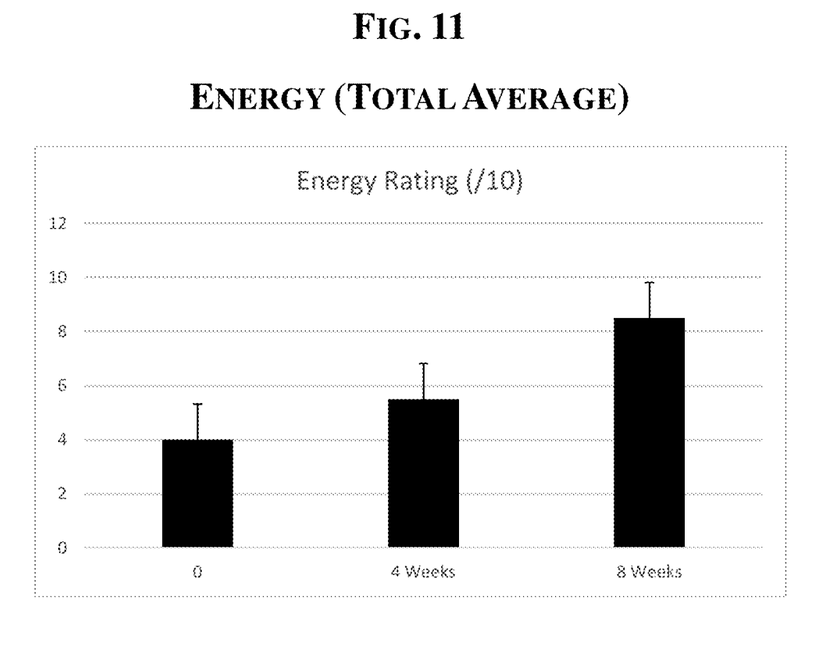
FIG. 11 shows energy (total average) results from the study of the four herb combination stated herein with standard deviations.

Significant improvements (i.e., reductions) were observed in scores for sleep onset and sleep maintenance, with energy levels increasing over the course of the trial. Means scores for each of the measures are shown in FIGS. 9-11. Furthermore, FIGS. 9, 10, and 11 display the standard deviations (SD), which demonstrates the measurement for the group spread out from the average (mean), illustrated by the bars on the graph. The standard deviation is denoted below using the +/- sign. The standard deviation was determined by providing a mean value for a series of values, in which the difference between the value and the mean value was calculated for each of the values of the group. Lastly, the weighted differences are summed and divided by an appropriate predetermined number to obtain the group spread from the average.

When analyzing the data as total average score, sleep onset improved from 45-minutes (with SD of +/-12) before falling asleep at the start of the trial to 28 minutes (with SD of +/-10) at 4 weeks and 12 minutes (with SD of +/-9) at 8 weeks, which was a statistically significant, 74% reduction, as illustrated in FIG. 9.

FIG. 10 illustrates sleep maintenance (total average) where at the start of the trial participants awoke 6 times (with SD of +/-1.6) throughout the night, on average. This was reduced to 3 (with SD of +/-1.7) times at 4 weeks and once a night (with SD of +/-1.0) at 8 weeks, which was a statistically significant, 83% reduction in waking episodes per night.

FIG. 11 illustrates the energy levels (total average) of the participants. Energy was self-rated by participants on a scale of 1 to 10 with 10 being the highest and/or best energy level. The total average energy rating was 4 (with SD of +/-1.2) at the start of the trial, increasing to 5.5 (with SD of +/-1.5) at 4 weeks and 8.5 (with SD of +/-1.4) at 8 weeks, which is a statistically significant, more than double the energy at completion of the trial.

Figure 12:
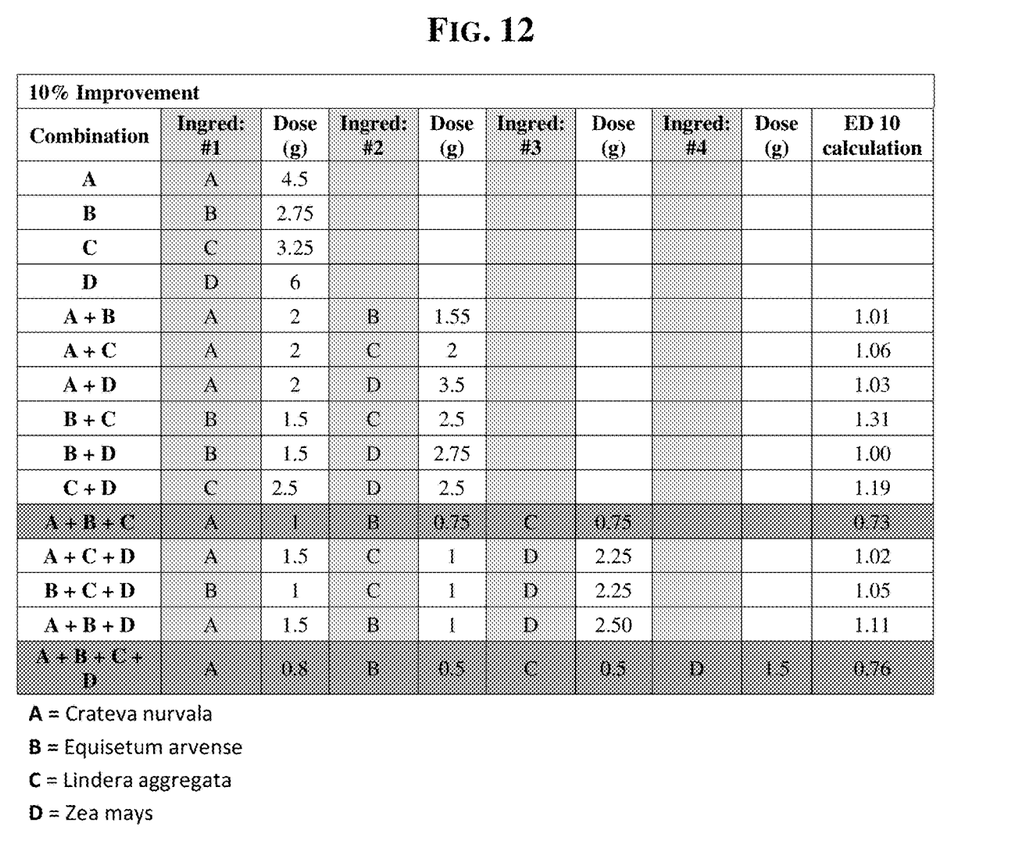
FIG. 12 shows the results of the median effective dose (ED10) for the various different combinations of the herbs indicated.
Figure 13:
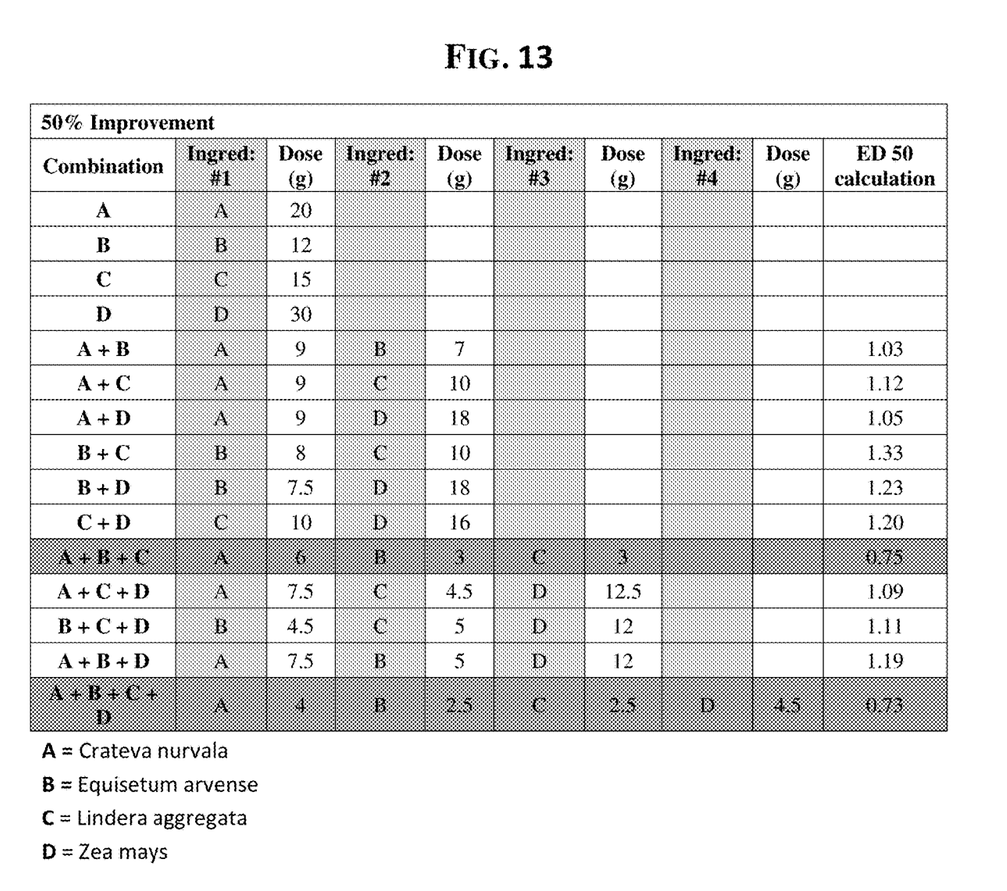
FIG. 13 shows the results of the median effective dose (ED50) for the various different combinations of the herbs indicated.
Figure 14:
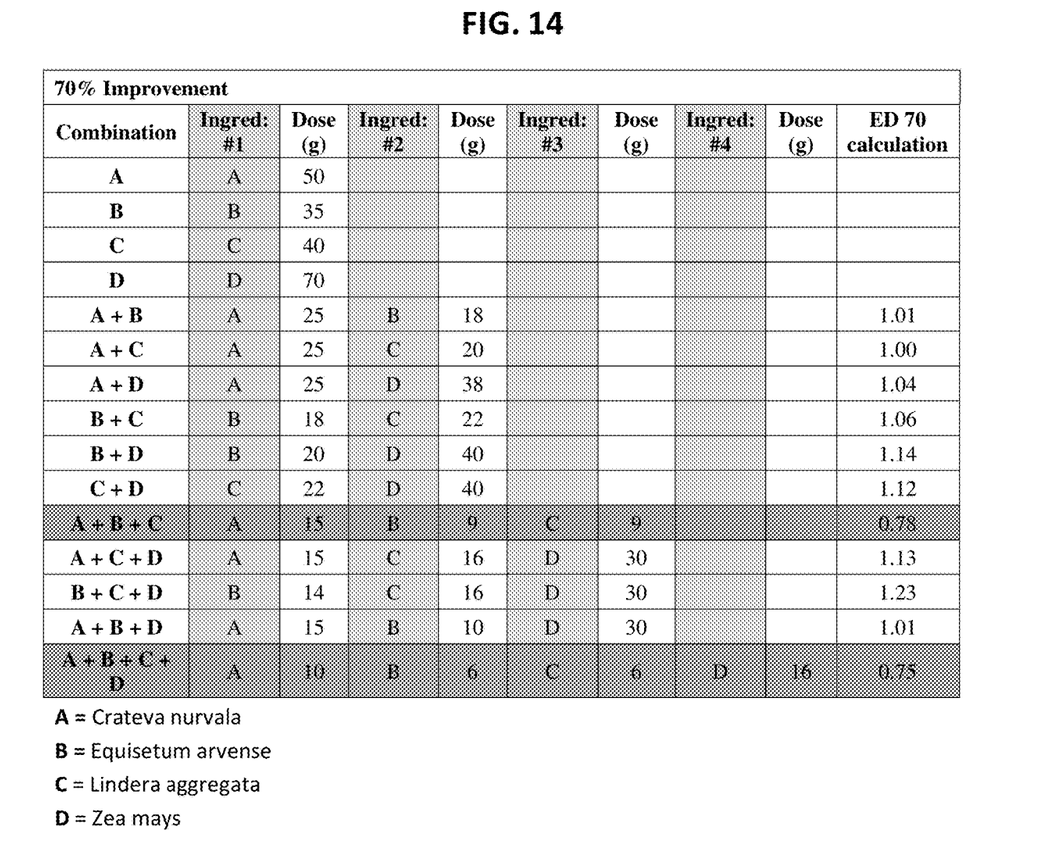
FIG. 14 shows the results of the median effective dose (ED70) for the various different combinations of the herbs indicated.

In yet another embodiment, the claimed composition was further tested to demonstrate the amount of sleep and motivation improvements, increased energy levels and benefits incurred by an individual using the claimed compositions. In relation, the claimed compositions were also compared to a variety of different herbal combinations, as illustrated in FIGS. 12-14, that included one, two, three, and four herb combinations. The results demonstrate that the claims compositions act synergistically to provide the benefits and advantages described herein.

FIGS. 12-14 list all the different possible one, two, three and four herb combinations used to achieve a 70%, 50%, and 10% improvements in sleep. As illustrated in FIGS. 12-14, the claimed compositions were proven synergistic by having a value less than 1, using the median effect equation as stated above. However, the values for the different one, two, three and four herb combinations resulted in a number that was greater than 1 to achieve the 70%, 50%, and 10% improvements.

The outcome of this trial demonstrates that the combination of *Crateva nurvala, Equisetum arvense* (Horsetail), *Lindera aggregata*, and *Zea mays* (Cornsilk) significantly improves sleep onset and sleep maintenance, as well as increasing daytime energy levels. The four herb combination serves as an effective treatment, with minimal side-effects.

For example, the four herb combination was used to treat three separate individuals, each at a different age with varying problems. The following are cases of how the four herb combination has improved the sleep onset, sleep maintenance, and energy of these individuals.

In the first case, a 57-year-old woman had a workplace arm injury one year previously and at the time found that the pain significantly impacted her sleep, with her sometimes sleeping for only 3 hours in the night. She took Codeine and Paracetamol for 3 months, gradually reducing the dose whilst undergoing physiotherapy. The physiotherapy continued for approximately 6 months until the arm was fully functional and pain-free. One year after the original injury, her sleep was still impaired with onset and maintenance insomnia. The woman stated that she "dreaded bedtime" and the hours she would be lying awake in bed. She worried during the day, with the worry increasing in the evening. She did not want to take sleeping medications but tried a variety of sedative and anxiolytic herbal treatments (including Valerian, Chamomile, and Passionflower) with little effect. In addition, she had changed her lifestyle avoiding commitments in the morning, and not socializing at night as she was worried that the stimulation would further impair her sleep. After 2 weeks on the herbal combination she noticed improvements. At 1 month, she was falling asleep within 20 minutes (versus over an hour before starting the treatment) and was waking up only once per night (versus 3 times or more before starting treatment). After 2 months of treatment she was falling asleep within 10 minutes and sleeping through most nights. Her quality of life was greatly improved and she felt confident to start socializing again (in the evenings) as well as committing herself more in the mornings.

In the second case, a 63-year-old male was presented with anxiety, worry and poor sleep. He stated that he felt nervous and anxious most of the time and was no longer confident talking to people, especially if he didn't know them very well. He further stated that over the past year he was feeling increasingly tired during the day, was less interested in meeting with friends or interacting with his family (pathology tests were within the normal range) and found conversations being too much of an effort. In addition, he would wake up 3 times during the night and walk. At 1 month of use, his night-time waking occurred only once each night and at 8 weeks he was sleeping through most nights. This was a huge improvement for him and for the first time in a year he felt normal. In addition, his concern and worry responses improved over the 2 months of treatment moving from rating them as occurring "a very great deal" (rating 6), at the start of the treatment, to "a little bit" (rating 2) after 2 months of treatment.

In the third case, a 79-year-old male presented with a disturbed sleep that was worsening over time. His pattern was to readily fall asleep but then wake up 6 times throughout the night which led to urinating half the time, and then having difficulty returning to sleep. Although he found some improvement with prostate medication (Flomax, Tamsulosin) in reducing his night-time urination his waking at nights was not reduced. While he was a retired man and did not have to wake up early, he spent 12 hours or more in bed just to feel remotely rested. He commented, "Lack of sleep impairs me greatly . . . decreases my ability to exercise the next day . . . I find my relationships are being affected, mainly because of the tiredness." Furthermore, to try and assist these issues he changed his lifestyle by avoiding water and caffeine intake, in the afternoon and abstained from drinking alcohol. He was worried and stopped exercising as a result of daytime fatigue; he worried that his condition would not improve given his age. At 1 month of use, his night-time waking reduced from 6 times to 3 times a night. At 8 weeks, his night-time waking reduced to 2 times and he was able to return to sleep easily, his daytime energy increased and he was more motivated to socialize.

As discussed herein, in yet another embodiment, the *Crateva nurvala, Equisetum arvense, Lindera aggregata* and *Zea mays* combination resulted in further improvements in sleep onset, sleep maintenance, and energy levels over the 8 weeks of treatment. There was an 83% improvement in sleep maintenance (average of 6 wakings per night reduced to once per night) and 74% improvement in sleep onset (average of 45 minutes reduced to 12 minutes). In addition, there was a total average increase in energy levels from a rating of 4/10 to 8.5/10 after 8 weeks of treatment. This is a 112.5% increase, or more than doubling of energy levels. As poor sleep and associated low energy are known to impair socializing, exercising and quality of life, the improvement in sleep and energy levels seen with this formulation will also result in improvements in social interactions and improvement in the quality of life.

What is claimed is:

1. A method for improving sleep and social interaction and reducing concern or worry in mammals, the method comprising:
   administering an effective amount of a composition to a mammal in need thereof comprising an extract of at least two ingredients selected from:
   *Equisetum arvense;*
   *Zea mays;*
   *Crateva nurvala*; and
   *Lindera aggregata;*
   wherein the composition is formulated as an oral dosage unit selected from one of a tablet, capsule and caplet.

2. The method of claim 1, wherein the effective amount is about 190 mg to 2400 mg daily.

3. The method of claim 1, wherein the composition is administered for about 8 weeks.

4. The method of claim 1, wherein the *Lindera aggregata* is standardized.

5. The method of claim 1, wherein the *Crateva nurvala* is standardized.

6. A method for improving energy and social interaction and reducing concern or worry in mammals, the method comprising:

administering an effective amount of a composition to a mammal in need thereof comprising an extract of at least two ingredients selected from:

*Equisetum arvense;*
*Crateva nurvala;*
*Lindera aggregata;* and
*Zea mays,*
wherein the composition is a tablet, capsule or caplet.

7. The method of claim 6, wherein the effective amount is about 282 mg to about 3200 mg daily.

8. The method of claim 6, wherein the period is about 8 weeks.

9. The method of claim 6, wherein the composition is comprised of an extract of *Equisetum arvense, Crateva nurvala, Lindera aggregata,* and *Zea mays*.

10. The method of claim 6, wherein the *Lindera aggregata* is standardized.

11. The method of claim 6, wherein the *Crateva nurvala* is standardized.

12. The method of claim 6, wherein the *Zea mays* is standardized.

13. The method of claim 8, wherein the composition is administered for about eight weeks.

\* \* \* \* \*